United States Patent [19]
Kulisz et al.

[11] Patent Number: 5,437,604
[45] Date of Patent: Aug. 1, 1995

[54] NONSURGICAL INTRAURETHRAL BLADDER CONTROL DEVICE

[75] Inventors: Andre A. Kulisz; Valery Migachyov, both of San Antonio, Tex.

[73] Assignee: HK Medical Technologies, Incorporated, San Antonio, Tex.

[21] Appl. No.: 298,033

[22] Filed: Aug. 30, 1994

Related U.S. Application Data

[63] Continuation-in-part of Ser. No. 173,636, Dec. 23, 1993.

[51] Int. Cl.⁶ ............................................. A61F 2/02
[52] U.S. Cl. .................................................. 600/30
[58] Field of Search ................................. 600/29-31

[56] References Cited

U.S. PATENT DOCUMENTS

| | | | |
|---|---|---|---|
| 3,731,670 | 5/1973 | Loe | 600/30 |
| 3,812,841 | 5/1974 | Isaacson | 600/29 |
| 4,553,533 | 11/1985 | Leighton . | |
| 4,679,546 | 7/1987 | van Waalwijk van Doorn et al. . | |
| 4,934,999 | 6/1990 | Bader | 600/29 |
| 4,955,858 | 9/1990 | Drews | 604/8 |
| 4,968,294 | 11/1990 | Salama | 600/30 |
| 4,969,474 | 11/1990 | Schwarz . | |
| 5,007,894 | 4/1991 | Enhorning | 600/29 |
| 5,007,898 | 4/1991 | Rosenbluth et al. | 604/54 |
| 5,012,822 | 5/1991 | Schwarz . | |
| 5,041,092 | 8/1991 | Barwick | 600/29 X |
| 5,078,676 | 1/1992 | Bailly | 600/31 |
| 5,088,980 | 2/1992 | Leighton | 600/30 |
| 5,090,424 | 2/1992 | Simon et al. . | |
| 5,097,848 | 3/1992 | Schwarz . | |
| 5,112,306 | 5/1992 | Burton et al. | 604/101 |
| 5,114,398 | 5/1992 | Trick et al. | 600/29 |
| 5,123,428 | 6/1992 | Schwarz . | |
| 5,140,999 | 8/1992 | Ardito | 600/29 X |

*Primary Examiner*—Angela D. Sykes
*Attorney, Agent, or Firm*—Nawrocki, Rooney & Sivertson

[57] ABSTRACT

An improved self contained automatic bladder control device includes a valve assembly mount for releasably receiving a valve assembly. The preferably cylindrical mount has a textured outer surface designed to interact with urethral tissue. Thus the mount can be placed nonsurgically into a urethra and in time it will be held against movement by the tissue interaction with the textured outer surface, yet the mount will still be removable without surgery. Two embodiments of valve assemblies are disclosed, each of which provides a sphincter-like operation of the bladder control apparatus. A first embodiment is designed to use Bernoulli's law to hold open the valve apparatus after a short period of muscle contraction. The second embodiment is designed to use the fact that the force generated by hydrostatic pressure is directly related to the area on which it impinges, to accomplish the desired valve holding period.

8 Claims, 12 Drawing Sheets

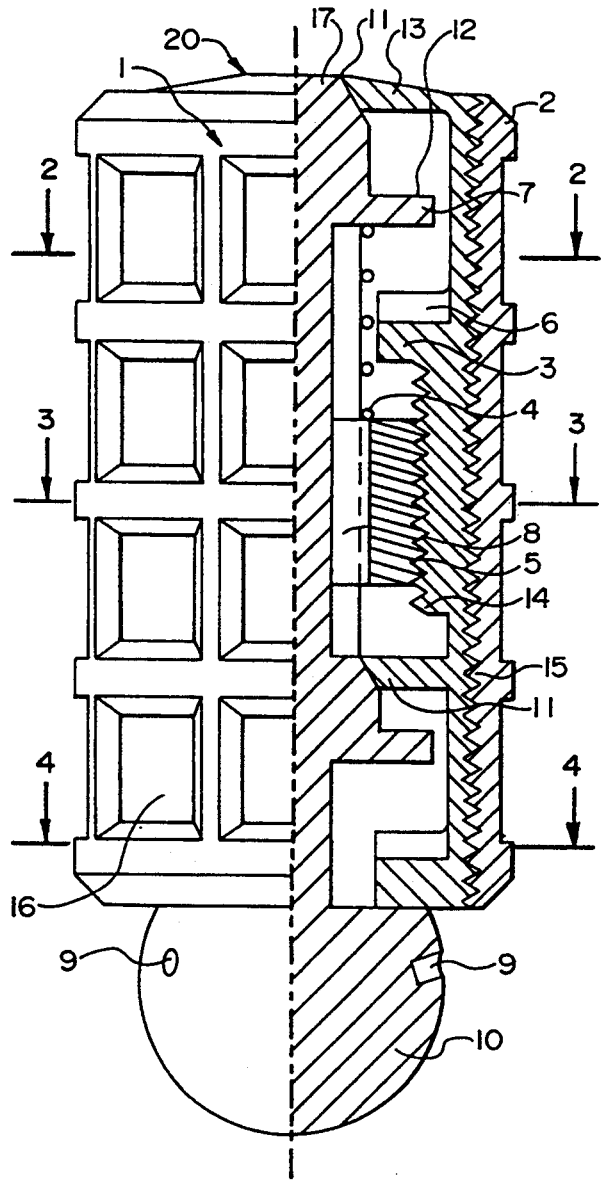
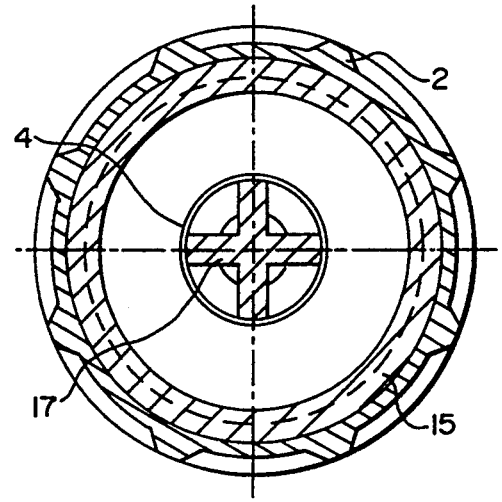
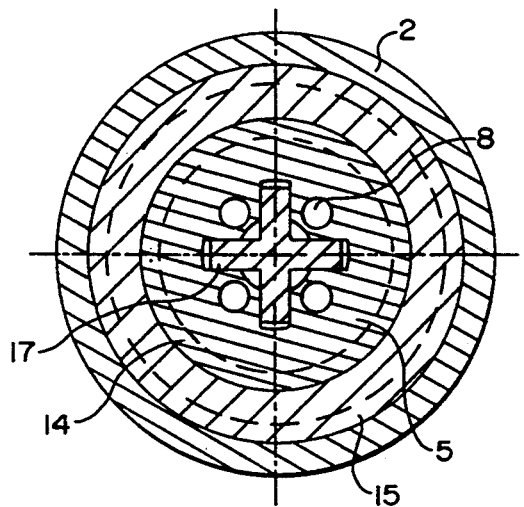

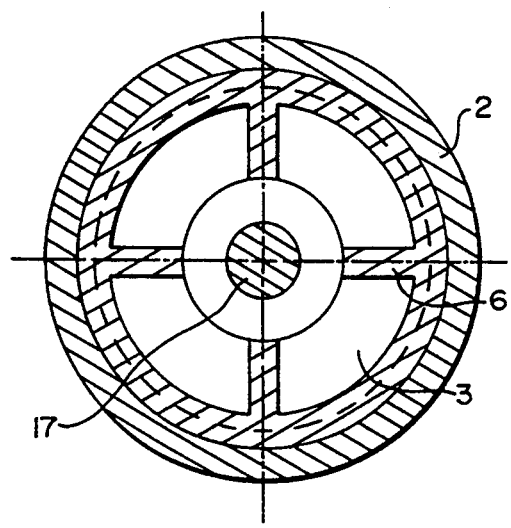
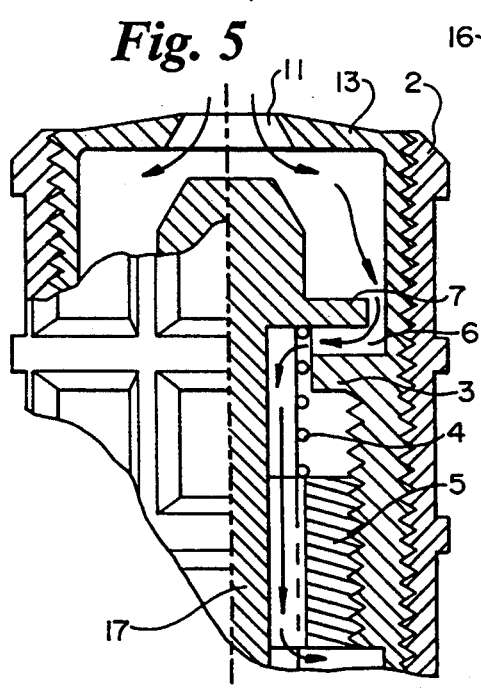
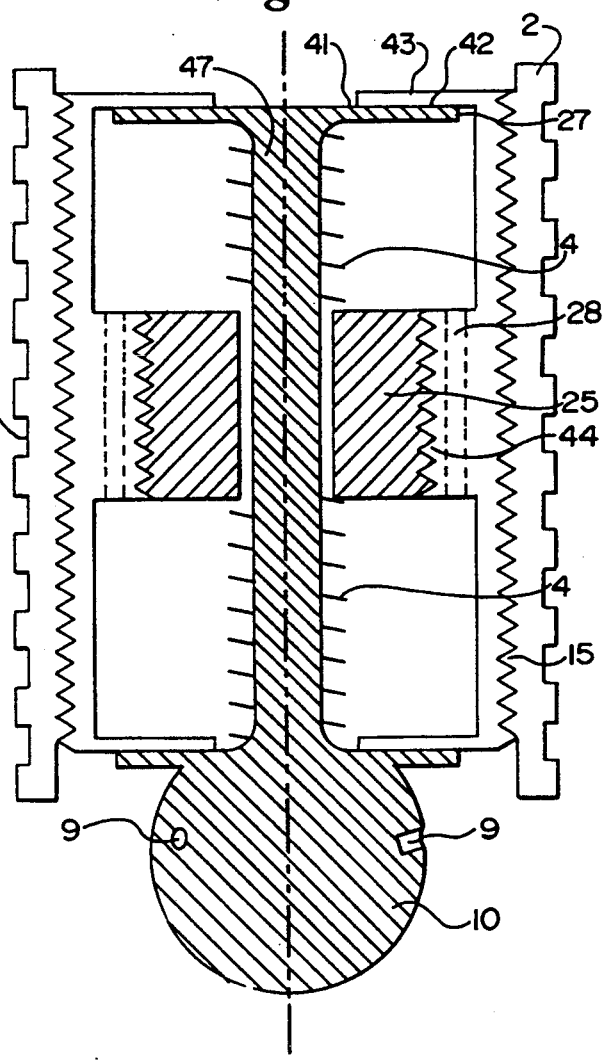
Fig. 4
Fig. 5
Fig. 6

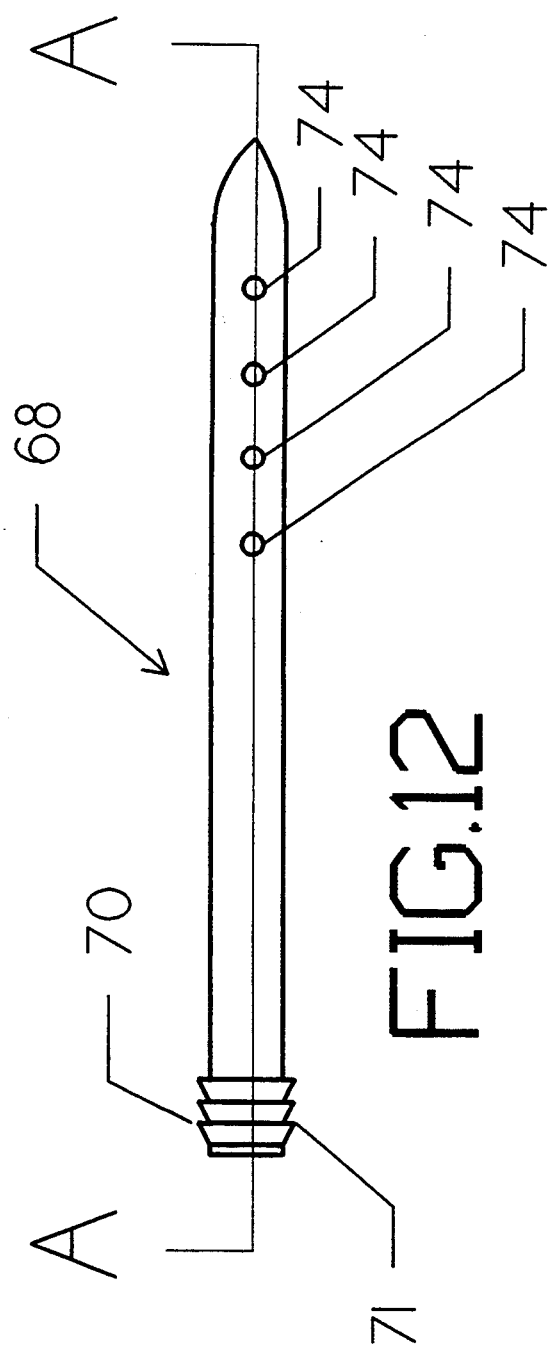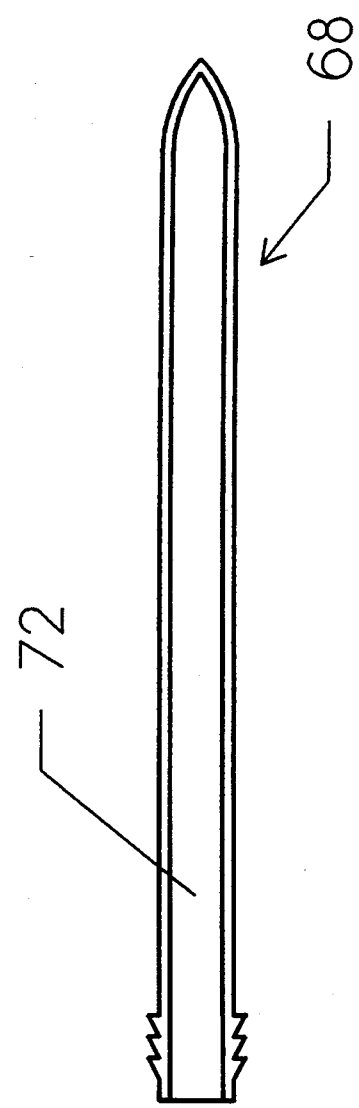

NONSURGICAL INTRAURETHRAL BLADDER CONTROL DEVICE

RELATED APPLICATIONS

This application is a continuation-in-part of U.S. patent application Ser. No. 08/173,636, filed Dec. 23, 1993.

BACKGROUND OF THE INVENTION

1. Field of the Invention

The present invention generally relates to the field of medical devices and more particularly to bladder control devices, and still more particularly to an intraurethral bladder control apparatus commonly referred to as an artificial sphincter.

2. Description of the Prior Art

The use of various sphincter and bladder control devices is wide spread in the field of the present invention. The use of intraurethral valving apparatus is also well known in the art, as evidenced by, for example, U.S. Pat. Nos. 4,553,533; 4,679,546; 4,969,474; and 5,123,428. In general terms, it is the goal of the prior art and the present invention to provide a valving system for a patient's bladder, which system is placed directly in the urethra and adjacent the bladder. The valving system is ideally turned on by the patient and turned off when the bladder has been sufficiently emptied.

Some of the problems and disadvantages found in the prior art include: the need for surgical implantation and removal of the device in the urethra; the susceptibility of the device to leakage or to undesired valve openings; the failure of the valve device to stay open long enough to provide complete emptying of the bladder; and in some prior art devices the need for an additional external product, such as a magnet, to actuate the valve device.

SUMMARY OF THE INVENTION

The apparatus and method of this invention overcomes these potential disadvantages by providing an improved intraurethral bladder control apparatus which includes a valve assembly, and a valve assembly mount for releasibly holding the assembly and adapted to be nonsurgically placed and releasibly held in the urethra of a patient. The mount is provided with a textured outer surface to which urethral tissue will conform to hold the mount at a selected position therein. The valve assembly cooperates with apparatus in an inner chamber of the mount for releasable installation of the assembly. The mount is preferably generally cylindrical in shape with a generally cylindrical inner chamber or lumen where valve assembly holding apparatus is deployed.

Each of the preferred embodiments of the valve assembly has adjustment apparatus operable whether the assembly is in the valve assembly mount or not, for positioning the assembly and for setting desired values of the opening and closing the valve, and for a fail-safe mode which is a feature of each preferred embodiment.

Each preferred embodiment of the present invention also includes apparatus for assuring that once opened by the patient's own abdominal muscle contraction, the valve stays open for a sufficient time to empty the bladder, and then closes without further action by the patient. A first preferred embodiment includes a design to utilize Bernoulli's principle to provide a negative pressure that holds the valve open during fluid flow, and a second preferred embodiment is designed to utilize a valve area enlargement during fluid flow to keep the valve open.

Additional apparatus for sizing the mount, and for inserting and removing the mount is incorporated into this invention. Pressure apparatus for providing either a liquid, jell or a gas lubricant under pressure is part of this additional apparatus. A number of probes of various sizes, each of which have a lumen extending from the proximal end to sets of aligned holes spaced about the circumference near the distal end, provide a passage for the lubricant. The pressure apparatus is attached to the proximal end of a probe. This provides lubricant about the distal end of the probe. This lubricant aids in inserting probes into the urethral opening in sequence, from the smallest size to the largest size the urethra will accept, to determine the urethra size. This information is necessary to determine the proper mount size.

This same pressure apparatus is used to provide pressurized lubricant adjacent to the base of the mount for placing the mount within the urethra or for removing the mount from the urethra. A retriever, which threads into a mating hole in the base of the mount, has a shoulder at its distal end adjacent to the mount. The retriever has a lumen from the proximal end which communicates with holes spaced about the circumference of the shoulder. The retriever has means at the proximal end for connecting the pressure apparatus. With the pressure apparatus connected to the proximal end of the retriever and the retriever threaded into the base of the mount, the retriever can introduce lubricant under pressure at the base of the mount.

A sleeve with flanges near each end slideably encircles the retriever. This sleeve, when placed over the retriever and pressed against the patient's body, will seal the pressurized lubricant within the urethra. This pressurized lubricant will expand the urethra from the base of the mount inward. This will free the urethra from the textured outer surface of the mount for insertion or removal. The pressurized lubricant will also flow from the base of the mount into this expanded area around the mount to provide lubricant for insertion or removal of the mount. This process is particularly critical when removing the mount, since the walls of the urethra adhere to and tightly engage the textured walls of the mount after installation.

BRIEF DESCRIPTION OF THE DRAWINGS

The above described as well as other objects and many of the attendant advantages of the present invention will be readily appreciated as they become better understood by reference to the following detailed description when considered in connection with the accompanying drawings, in which like reference numerals designate like parts throughout all figures:

FIG. 1 is a partial sectional view of a first embodiment of the intraurethral bladder control apparatus of this invention with the valve closed;

FIG. 2 is a cross-sectional view of FIG. 1 taken along the line 1—1;

FIG. 3 is another cross-sectional view of FIG. 1 taken along the line 2—2;

FIG. 4 is yet another cross-sectional view of FIG. 1 taken along the line 3—3;

FIG. 5 is a partial sectional view of the embodiment of FIG. 1 with the valve open;

FIG. 6 is a cross-sectional view of a second embodiment of the apparatus of this invention with the valve closed;

FIG. 12 is a side view of a probe;

FIG. 12A is a cross-sectional view of FIG. 12 taken along the line A—A.

DETAILED DESCRIPTION OF THE PREFERRED EMBODIMENTS

Figure 8:
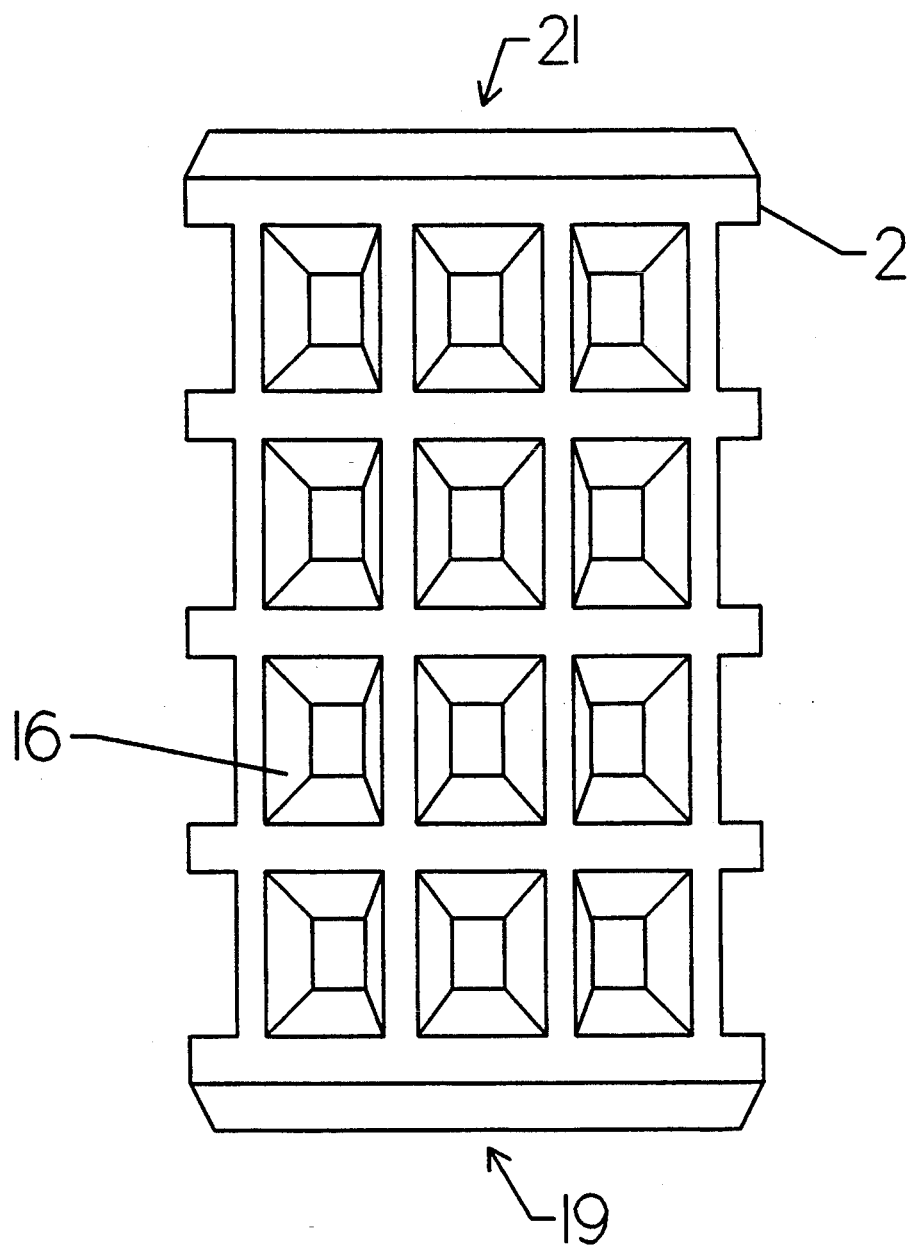
FIG. 8 is a plan view of the valve assembly mount of this invention.

Referring first to FIG. 8 there is shown a valve assembly mount 2 in the preferred form of a cylinder having a textured outer surface 16 designed to interact with urethral tissues such that mount 2 may be nonsurgically and releasibly positioned in a patient's urethra. Mount 2 includes a valve orifice indicated at 11 and adapted to be positioned adjacent the patient's bladder exit, and an assembly orifice indicated at 19 adapted to receive a valve assembly for internal mounting. As disclosed and more fully described in other figures of the drawings, the interior of mount 2 includes connection apparatus for releasibly and adjustably mounting a valve assembly. In practice, mount 2 is positioned in the patient's urethra first, left for a period of time to enable the urethra tissue to conform to the textured outer surface 16 of mount 2 to hold mount 2 securely in place, and then a valve assembly is mounted in mount 2.

Figure 9:
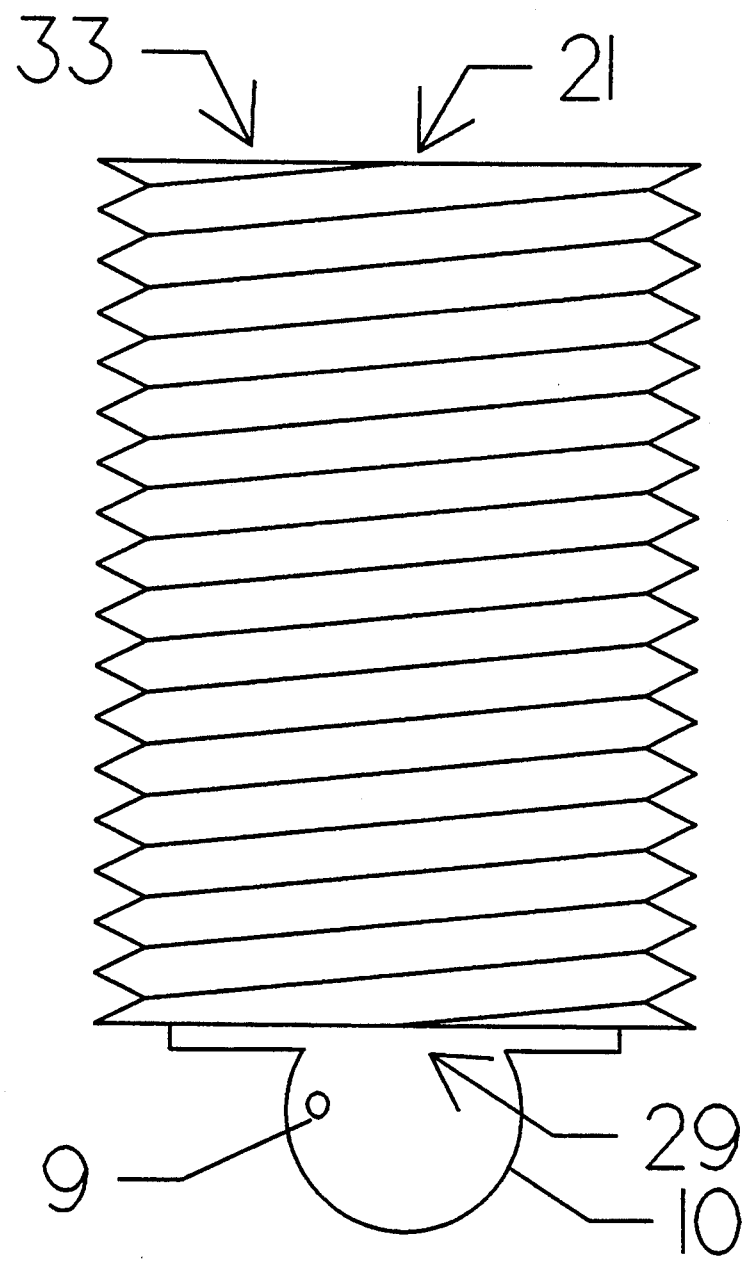
FIG. 9 is a plan view of a valve assembly of this invention.

In FIG. 9 there is shown a valve block 33 adapted to releasibly receive a valve apparatus in a manner fully described below with reference to other figures of the drawings. Block 33 is shown as preferably having a threaded outer surface designed to match a threaded inner surface (not shown in FIG. 8) of mount 2. Block 33 also has a valve orifice indicated at 21 for alignment adjacent to orifice 11 of mount 2, and an apparatus receiving orifice indicated at 29 for insertion of a valve apparatus.

As can be seen in FIG. 9, when a valve apparatus is in place within block 33, an adjustment device 10 having lock notches 9 will be available outside block 33. By using an appropriate adjustment tool (not shown) to lock into notches 9, device 10 may be rotated to make a plurality of adjustments more fully described below with reference to other figures of the drawings.

Referring now to FIG. 1 there is shown a first embodiment of the bladder control apparatus 1 of this invention, including cylindrical valve assembly mount 2 having textured outer surface 16 and a valve assembly 20 which is threaded into mount 2 by means of a connection thread 15. Valve assembly 20 includes a valve block 13, a valve 17, a valve orifice 11, a valve ring 7 having a valve area 12, a coiled spring or other biasing apparatus 4, a spacer 6, a stationary ring 3, a fluid passage 8, a bias adjustment apparatus 5, a thread 14 joining bias adjustment apparatus 5 to block 13, and adjustment device 10 having locking notches 9.

The cross-sectional views of FIGS. 2, 3 and 4, respectively taken along the lines 1—1, 2—2 and 3—3, more clearly depict the inner structure of device 1 of FIG. 1, clarifying the positioning and formations of valve 17, spring coil biasing device 4, bias adjustment means 5 with thread 14, fluid passages 8, stationary ring 3 and spacers 6.

In FIG. 1 valve 17 is in the closed position in orifice 11, thus preventing the flow of urine fluids from the bladder. With reference to FIG. 5, valve 17 is shown in the open position, removed from orifice 11, and a plurality of lines with arrows depict the fluid flow path through valve block 13.

In practice, valve assembly mount 2 is first inserted into a urethra and allowed to stay for a period of time (usually a few weeks) sufficient for the urethral tissue to conform to the textured outer surface 16 to thus essentially immobilize mount 2. After mount 2 is firmly held by the tissue, a valve assembly such as assembly 20 of FIG. 1 is inserted into the internal chamber or lumen of mount 2 where it is connected and adjusted.

Referring now to the first preferred embodiment of FIGS. 1-5 which utilize Bernoulli's principle to retain the valve in an open position, assume that assembly 20 has been mounted in the lumen of assembly mount 2 which has been immobilized in the patient's urethra in the manner described above. Block 13 is then adjusted within mount 2 such that orifice 11 passes through orifice 21, as shown in FIG. 8, to align with the output from the patient's bladder (not shown). As the bladder fills with urine, the resulting growth in the urine column exerts greater pressure on valve 17 through orifice 11 and at the same time the resulting growth in volume within the bladder stimulates the patient's need to void. To initiate the voiding process the patient need only contract the muscles of the lower abdominal cavity for a short period of a few seconds. This short period of contraction will increase the pressure on valve 17 long enough for it to move against the bias of spring 4 and thus begin the flow of urine through valve assembly 20 along the path shown by the arrows in FIG. 5.

As the urine flows in the path shown, valve 17 moves toward valve stop or rest 6. Rest 6 is a vertical element extending radially for separating the lower surface of valve ring 7 from stationary ring 3. The urine then flows around the edge of valve ring 7 and between the lower surface of ring 7 and stationary ring 3, such that a negative pressure is induced according to Bernoulli's principle between these two surfaces. This negative force overcomes the tension of spring 4 and holds ring 7 down against stop 6, thus holding valve 17 open, as long as a sufficient flow of urine is present. When the flow decreases below a sufficient amount, the negative force is decreased until the bias from spring 4 can again close valve 17 in orifice 11 to cut off the flow entirely.

The result of the actions as described in the preceding paragraph causes the desired holding pattern for the artificial sphincter device of this invention. That is, once valve assembly 20 has been opened by muscle contraction to allow fluid flow through block 13, the application of Bernoulli's law will automatically prevent closure of valve 17 without further muscle contraction until the bladder has emptied enough to significantly reduce the urine flow; and then the valve assembly will automatically close without further muscle effort. The patient's need to void will have been met by a simple, short initial contraction of the muscles of the lower abdominal cavity.

The force with which valve 17 is held closed or seated in orifice 11 is determined by the tension from spring 4, which may be any form of bias device. This tension or bias is adjusted by bias adjustment apparatus 5, best seen in FIGS. 1 and 3. To set the desired tension of coil 4, an adjustment tool (not shown) is passed through the urethra to grasp and lock into notches 9 of adjustment device 10. Device 10 is then selectively rotated which rotates valve 17 and bias adjustment means 5. The rotation of means 5 causes it to move up or down thread 14 to increase or decrease the tension of spring 4.

The rotation of valve 17 in the direction of reduced bias from coil 4 will eventually disable bladder control device 1 by removing valve 17 from is seat in orifice 11 to allow a free flow of fluid through block 13. Further rotation after reaching the point of free flow will cause rotation of block 13 to first change its positioning within mount 2 and eventually to cause it to disengage from mount 2 entirely. Replacement of block 13 into mount 2 is accomplished by simply reversing the direction of rotation of device 10.

The above description of the structure and operation of the preferred embodiment of FIGS. 1–3 which utilizes Bernoulli's law is applicable to patients who have a sufficiently rapid rate and volume of urine flow. These values can be clinically determined. If it is found that the patient does not meet the requirements for the use of the above described embodiment, the second preferred embodiment of this invention as described in FIGS. 6–7 can be used.

FIG. 6 again shows a valve assembly mount 2 in which a valve block 43 is removably positioned through use of threads 15. A valve 47 abuts against an orifice 41 and is maintained in the closed position by a coil spring or other bias device 4. In this embodiment valve 47 has a valve ring 27 with a valve surface area 42 significantly greater than the area of orifice 41. Coil 4 abuts against bias adjustment device 25 which is connected to block 43 via thread 44. Valve 47 is connected to adjustment device 10 which again carries locking notches 9. Fluid passages 28 are provided to pass urine through block 43 along a desired path.

Figure 7:
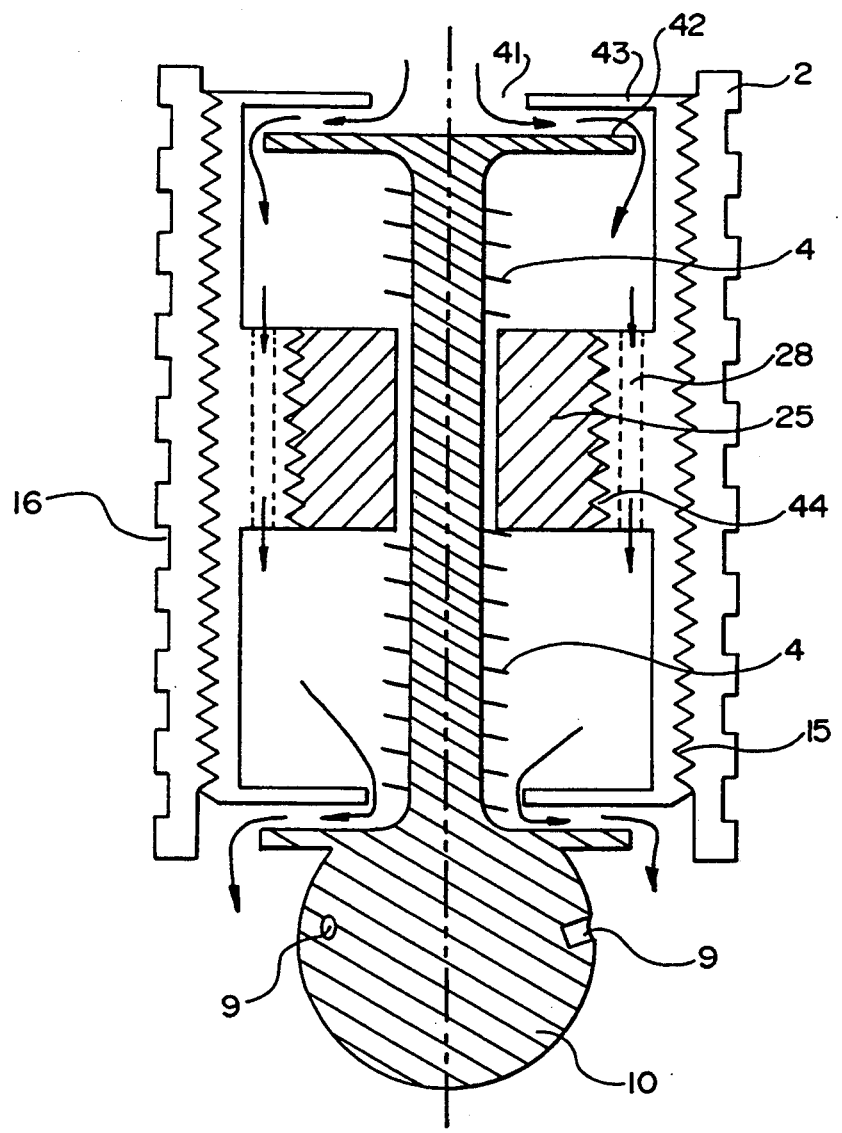
FIG. 7 is another cross-sectional view of the embodiment of FIG. 6 with the valve open.

In FIG. 6 valve 47 is shown as biased against orifice 43, thus closing valve block 43 to prevent urine flow. Referring now to FIG. 7 valve 17 is shown in the open position and the flow of urine through block 43 is depicted by the arrows.

In operation, mount 2 will have first been secured in the patient's urethra in the nonsurgical, removable manner described above with regard to FIGS. 1–5. Thus the urethral tissue will have conformed to surface 16 to hold mount 2 in place. Block 43 will then be threaded into mount 2 to place orifice 41 in the urethra adjacent to the patient's bladder. As the bladder fills the urine column will place increased pressure on valve 47 through orifice 41, as well as causing a need to void in the patient. To initiate operation of the device of this embodiment of the present invention the patient again need only contract the muscles of the lower abdominal cavity for a few seconds. This short period of contraction will cause sufficient pressure for valve 47 to open against the tension of coil spring 4.

As soon as valve 47 opens, the urine flow through orifice 41 will impinge on the full surface area 42 of valve ring 27, and since this area is greater than the area of orifice 41, valve 47 will remain open even after the contractions are released, until the urine column has been reduced to an acceptable small amount. The basis of this embodiment is the known fact that force generated by hydrostatic pressure is directly related to the area of impingement, that is, Force = Pressure × Area. Thus valve ring 27 and orifice 41 can be designed to follow the fact that if valve area increases n times, the pressure may decrease n times, and the force exerted on the valve will remain the same. By making ring 27 of sufficient surface area 42 relative to the area seen through orifice 41, valve 47 will be held open after muscle contraction ceases even in a patient with a relatively low flow rate through the urethra.

Valve 47 will remain open until the fluid pressure has dropped such that even the increased area is not enough to afford a multiple that will overcome the bias of coil 4, and then valve 47 will automatically be biased closed and remain closed until the bladder fills and the patient creates another contraction. Thus, as in the case of the first embodiment described above, this embodiment of the invention will also operate in a manner closely resembling the action of a normal sphincter muscle.

In both embodiments described above there are fail-safe measures designed into the bladder control device. By proper selection of the tension on the respective of valves 17 or 47 caused by bias apparatus 4, the valves can be made to open without muscle contraction as the pressure passes a certain level in the bladder. This can avoid serious problems caused by the increased bladder pressure should the patient not recognize the need to void or be unconscious, or the like. Further, again by proper adjustment of the bias spring, accidental turn-on of the bladder control device due to unexpected contractions, for example from a sneeze or cough. In general, if a proper spring tension is selected and the bladder is not overly full, valves 17 and 47 will remain seated until a contraction force of sufficient strength has been present for more than an instantaneous period of time, such as the time of a cough. This need for a short but sustained period of contraction prevents the device from entering its "automatic open" phase after an unexpected abrupt contraction.

Figure 10:
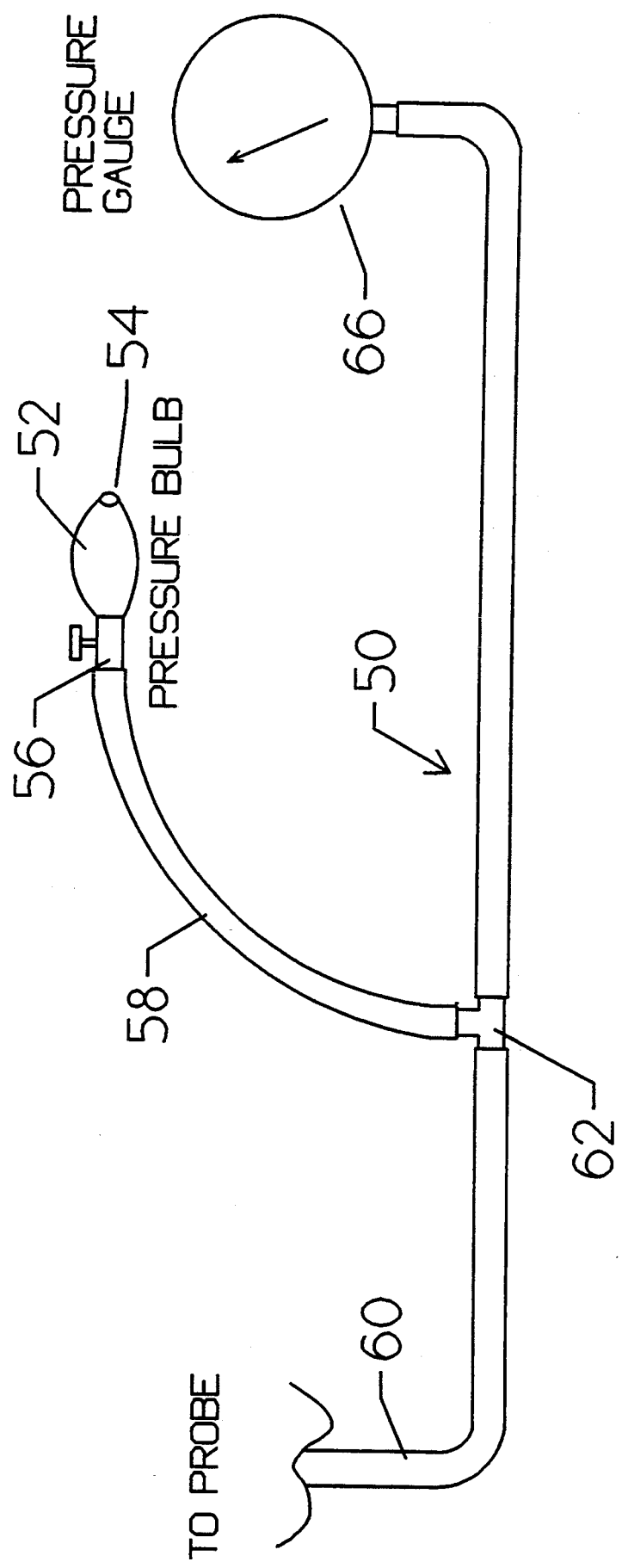
FIG. 10 is a plan view of pressure apparatus of this invention.

The additional apparatus for sizing the mount, and for inserting and removing the mount is shown in FIGS. 10 through 15A. Pressure apparatus 50 is shown in FIG. 10. Pressure apparatus 50 is used to provide a pressurized liquid, jell or a gas. Pressure apparatus 50 consists of a pressure bulb 52 having an gas intake opening 54 and a shut-off valve 56. A flexible proximal hose 58 and a flexible distal hose 60 both connect to T-connector 62. T-connector 62 is also connected by a third flexible hose to pressure gauge 66. Pressure gauge 66 provides necessary pressure information. Pressure is provided by squeezing bulb 52 until the desired pressure, as indicated by pressure gauge 66, is registered. At that time, valve 56 can be closed to retain pressure. If a jell or liquid is used as a lubricant, hose 60 is preloaded with the desired material. If gas is to be used as a lubricant it is introduced into intake 54 by supplemental equipment, not shown.

Probe 68 is shown in FIGS. 12 and 12A. Proximal end 70 of probe 68 has a series of ridges 71 extending around the circumference arranged and sized to engage the distal end of distal hose 60 from pressure apparatus 50 for attachment means to provide pressure to the probe. While ridges are shown in this embodiment any means that would provide a similar mechanical connection can be used to achieve the same result. Probe 68 has a distal end, a proximal end and a lumen 72 extending from the proximal end adjacent to but not completely to the distal end. Lumen 72 thus provides a passageway from the proximal end through probe 68 which is blocked on the distal end. Lumen 72 communicates with a number of distal holes 74 near the distal end of probe 68. Distal holes 74 are arranged in sets of three aligned with the longitudinal axis of probe 68. Several sets of these distal holes 74 are placed around the circumference of probe 68. The distal end of probe 68 is rounded for ease of insertion.

Figure 14:
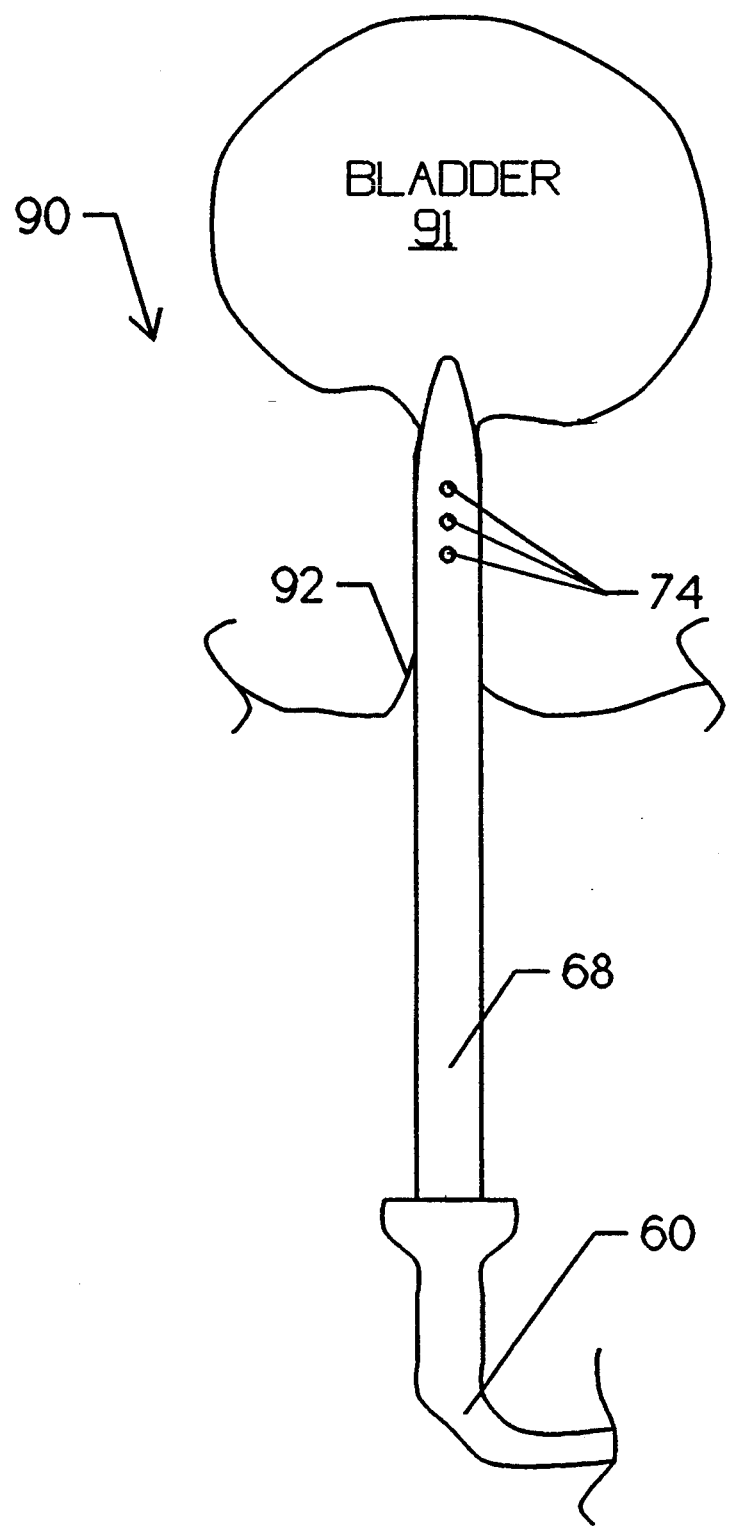
FIG. 14 is a fragmentary view of a patient showing the bladder and urethra in cross-section, with a probe in place within the urethra, and with the proximal end of the probe connected to the distal end of the distal hose of the pressure apparatus.

When the distal end of distal hose 60 from pressure apparatus 50 is connected to probe 68 and lubricating material within the apparatus is pressurized, as described earlier, this lubricating material will be forced into the probe through lumen 72 and outwardly through distal holes 74. This will assist in placing probe 68 within the urethra. This process is shown in FIG. 14. That portion of the patient's body 90, which is adjacent to and surrounding bladder 91 and urethra 92 is shown with probe 68 in place within the urethra.

Figure 16:
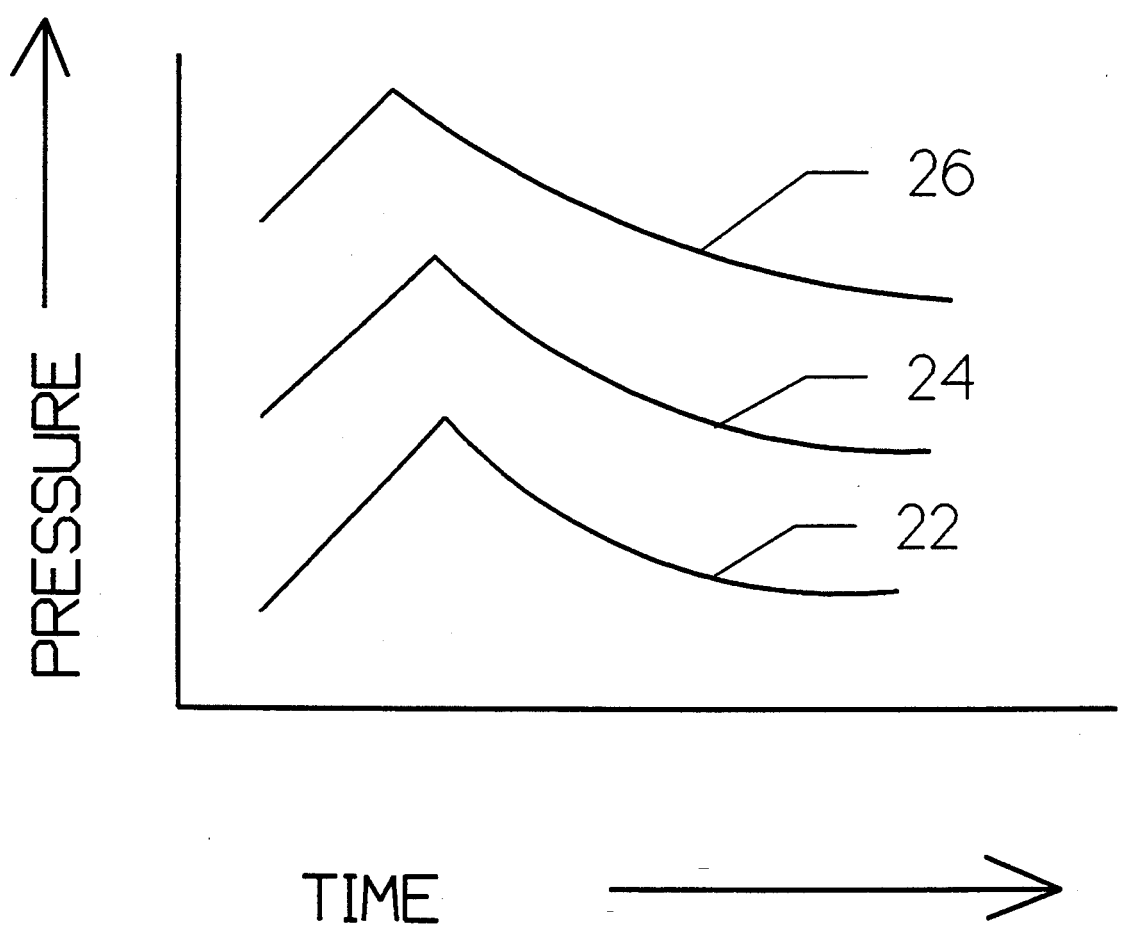
FIG. 16 is a pressure versus time diagram for three different probes.

A set of probes 68, ranging in diameter from 22 to 32 millimeters in steps of two millimeters is typical of those used to determine the diameter of the urethra. In FIG. 16 typical pressure curves for a probe having 22, 24 and 26 millimeter diameters, labeled 22, 24 and 26 respectively on the respective curves, are shown. These are typical curves obtained over time as pressure is applied to these probes. Knowledge of desirable pressure ranges permits the physician to select the appropriate diameter to be used for the mount.

Figure 11:
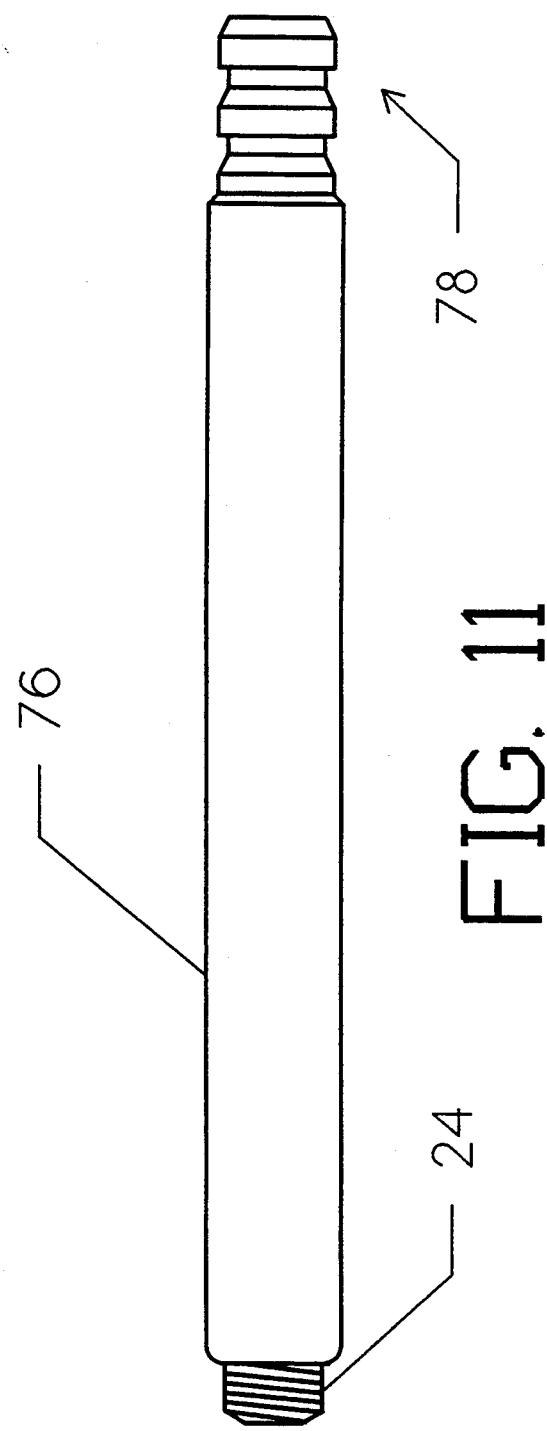
FIG. 11 is a side view of a retriever.
Figure 11A:
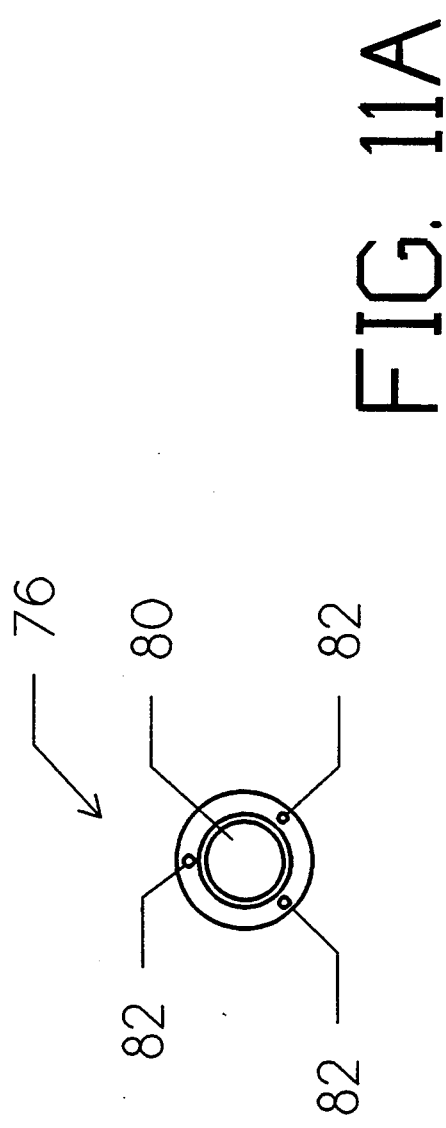
FIG. 11A is an end view of the retriever's distal end.

Retriever 76 is shown in FIGS. 11 and 11A. A series of grooves 78 about the proximal end of retriever 76 provides engagement means for the distal end of distal hose 60 from pressure apparatus 50. Retriever 76 has a distal end, a proximal end, a shoulder 77 around the distal end, and a lumen 80 extending from the proximal end through the retriever to the shoulder. Lumen 80 thus provides a passageway from the proximal end through receiver 76 blocked at the distal end. Lumen 80 communicates on the distal end of probe 76 with holes 82 around the circumference of shoulder 77. Holes 82 are located on shoulder 73 to ensure that lubricating material can pass freely from lumen 80 through holes 82 without being blocked by the walls of urethra 92.

Shoulder 77 has threads 84 about its circumference. Shoulder 73 and threads 84 are sized to fit within and mate with a threaded hole in the base of mount 2, not shown in this figure, to provide mechanical connection means between retriever 76 and mount 2 arranged such that the retriever is aligned with the mount. While a threaded connection is illustrated here, any mechanical connection that would attach the retriever to the mount with the same alignment and force would be acceptable for this use.

Figure 15:
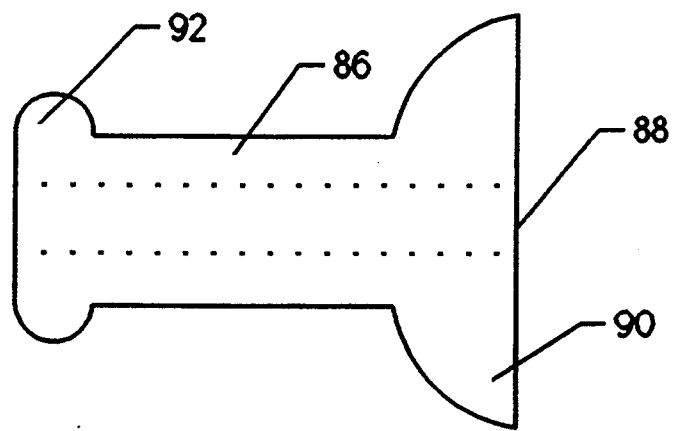
FIG. 15 is a side view of the sleeve.
Figure 15A:
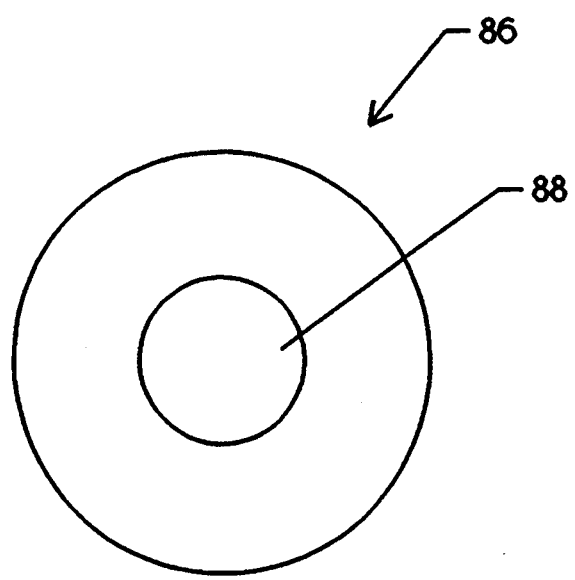
FIG. 15A is the end view of the sleeve's distal end.

Sleeve 86, shown in FIGS. 15 and 15A, has hole 88 extending completely through the sleeve from the smaller distal end 90 to the larger proximal end 92. Hole 88 is sized to fit slideably over retriever 76 such that little or no pressurized lubricant can flow between them.

Figure 13:
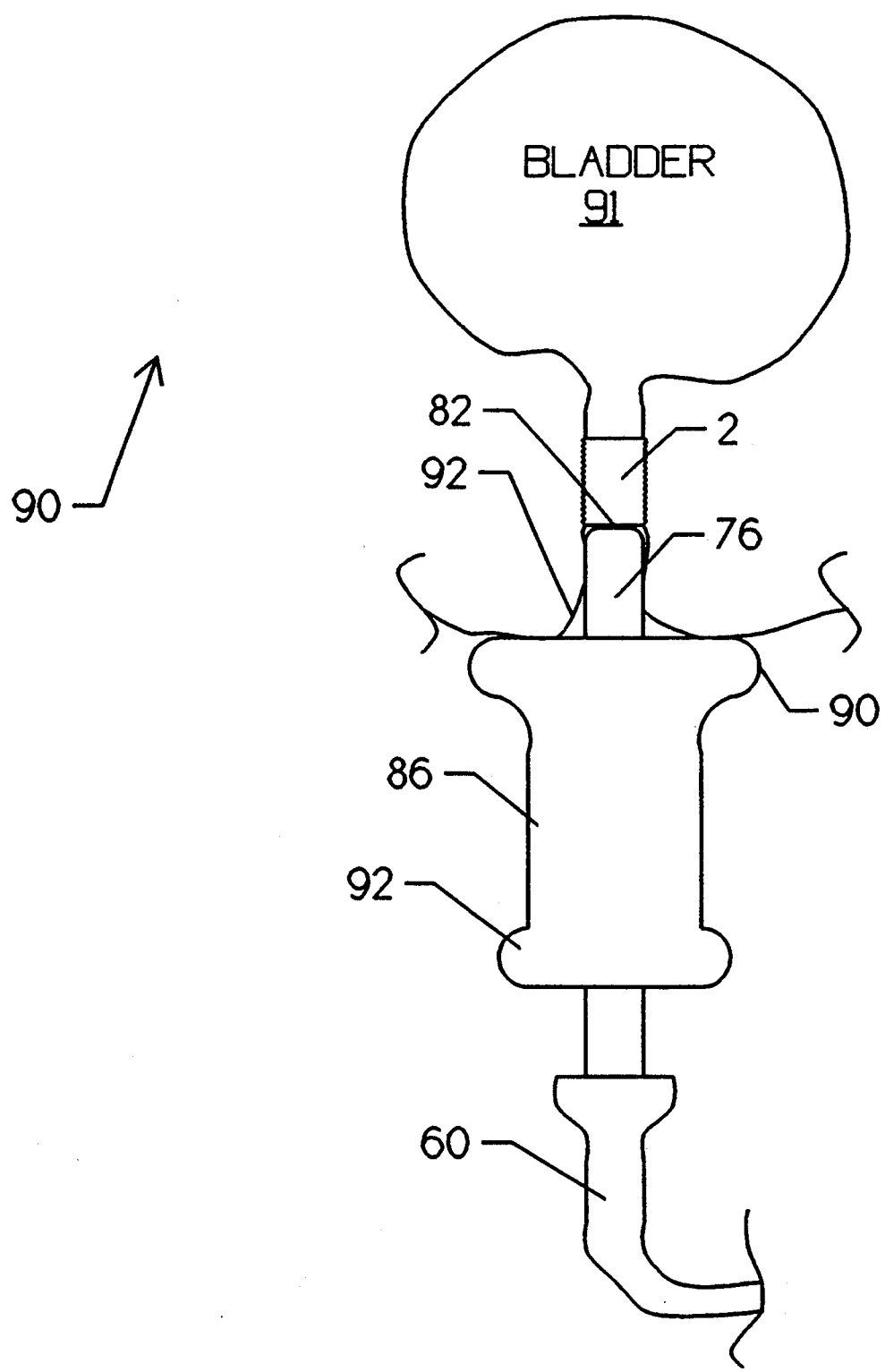
FIG. 13 is a fragmentary view of a patient showing the bladder and urethra in cross-section, with a mount, retriever and sleeve in place within the urethra, and with the proximal end of the retriever connected to the distal end of the distal hose of the pressure apparatus.

Sleeve 86 is used to contain pressurized lubricant within the urethra when mount 2 is being placed within or removed from urethra 92, as shown in FIG. 13. That portion of the patient's body 90, which includes bladder 91 and urethra 92, is shown with mount 2 in place within the urethra. Mount 2 has a threaded proximal hole which mates with thread 84 of retriever 76, described earlier, which holds the retriever securely in place as shown here.

In operation, with the apparatus arranged as shown in FIG. 13, with sleeve 86 positioned over probe 76 with the distal end 92 adjacent to the patient's body 90, lubricant can be introduced into urethra 92 through retriever 76. Distal hose 60 extending from pressure apparatus 50, not shown in this figure, provides lubricant through lumen 80 and distal holes 82 of retriever 86 to the volume between the shoulder 77 of the retriever and urethra 92. With sleeve 90 pressed against patient 90 and bulb 52 squeezed, the lubricant forced into urethra 92 will build in pressure and force the walls of the urethra outward. This both expands urethra 92 and simultaneously permits the lubricant to flow between the outer surface of mount 2 and the urethra.

In FIG. 13, mount 2 is already in place within urethra 92 and can be removed after lubricant has flowed completely around the mount, by pulling retriever 76 outward until the mount is freed. If mount 2 were being placed within urethra 92 the apparatus would be arranged exactly the same as before, excepting that the mount would be forced into urethra 92 using retriever 76, while lubricant from retriever 76 contained by sleeve 86, would assist in lubricating and expanding the urethra ahead of the mount.

Having thus described the preferred embodiments of the present invention, those of skill in the art will readily appreciate the other useful embodiments within the scope of the claims hereto attached.

We claim:

1. In bladder control apparatus adapted to be placed in a urethra and including a valve block having a valve with open and closed positions and a fluid flow path through the valve block, apparatus adapted for sizing the valve block for an individual patient comprising:
   a. pressure apparatus means for providing lubricant under pressure, said pressure apparatus means having a pressure gauge for determining lubricant pressure; and
   b. at least one elongated probe of predetermined diameter, each said probe having a proximal end, a distal end, and a lumen extending from the proximal end to near the distal end; each said probe having attachment means for attaching said pressure apparatus means to the proximal end thereof; and, each said probe further having a number of holes near the distal portion thereof communicating with said lumen.

2. Apparatus as in claim 1 wherein said pressure apparatus means comprises a pressure bulb having an intake port and an exhaust port, a proximal hose having a distal end and a proximal end, a distal hose having a distal end and a proximal end, a T-connector and a shut-off valve; said shut-off valve being attached between and controlling the flow between the exhaust port of said pressure bulb and the proximal end of said proximal hose; with the distal end of said proximal hose, the proximal end of said distal hose and said pressure gauge communicating with said T-connector; the distal end of said distal hose providing the pressure apparatus output.

3. Apparatus as in claim 1 wherein the distal end of said probes are rounded.

4. Apparatus as in claim 1 wherein the number of holes near the distal end of said probes are made up of sets of holes, each set consisting of a predetermined number of holes generally aligned with the longitudinal axis of said probe, said sets being distributed around the circumference of said probe.

5. Apparatus as in claim 1 wherein the attachment means for attaching the proximal end of said probe to said pressure apparatus means comprises a plurality of ridges of a predetermined size and shape formed around the circumference of said probe at the proximal end thereof, all portions of each ridge being a predetermined distance from the proximal end of said probe with the ridges being spaced an equal distance apart.

6. In bladder control apparatus adapted to be placed in a urethra and including a valve block having a valve with open and closed positions and a fluid flow path through the valve block, apparatus adapted for inserting and removing said valve block from the urethra comprising:
   a. pressure apparatus means for providing lubricant under pressure, said pressure apparatus means having a pressure gauge for determining the lubricant pressure; and
   b. an elongated retriever having a proximal end and a distal end, said distal end having a shoulder formed around the circumference thereof, said retriever also having a lumen extending from the proximal end thereof to said shoulder, said shoulder having a number of holes about the circumference thereof communicating with said lumen; said retriever also having attachment means for attaching the distal end of said retriever to the proximal end of a mount such that the retriever is aligned with the mount; said retriever further having attachment means for attaching said pressure apparatus to the proximal end of said retriever, and
   c. a sleeve having a proximal end, a distal end and a lumen extending from the proximal end to the distal end, said lumen being sized such as to slideably engage said retriever, said distal end of said sleeve having a flange around the circumference thereof, said flange and said lumen being sized such that when said retriever is placed within the urethra of a patient and said sleeve is forced against the patient, said flange will essentially seal the urethral opening around said retriever.

7. Apparatus as in claim 6 wherein said pressure apparatus means comprises a pressure bulb having an intake port and an exhaust port, a proximal hose having a distal end and a proximal end, a distal hose having a distal end and a proximal end, a T-connector and a shut-off valve; said shut-off valve being attached between and controlling the flow between the exhaust port of said pressure bulb and the proximal end of said proximal hose; with the distal end of said proximal hose, the proximal end of said distal hose and said pressure gauge communicating with said T-connector; the distal end of said distal hose providing the pressure apparatus output.

8. Apparatus as in claim 6 wherein said attachment means for attaching the distal end of said retriever to the proximal end of a mount comprises a thread around the shoulder of said retriever.

* * * * *